US00PP37669P2

(12) United States Plant Patent
Byrne et al.

(10) Patent No.: US PP37,669 P2
(45) Date of Patent: Sep. 8, 2026

(54) PEACH TREE NAMED 'TRH2E121L'

(50) Latin Name: *Prunus persica*
Varietal Denomination: TRH2E121L

(71) Applicant: The Texas A&M University System, College Station, TX (US)

(72) Inventors: David H. Byrne, Bryan, TX (US); Natalie Anderson, Calvert, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 19/336,358

(22) Filed: Sep. 22, 2025

(51) Int. Cl.
*A01H 6/74* (2018.01)

(52) U.S. Cl.
USPC ..... Plt./197
CPC ..... *A01H 6/7463* (2018.05)

(58) Field of Classification Search
USPC ..... Plt./197
CPC ..... A01H 5/0868
See application file for complete search history.

(56) References Cited

U.S. PATENT DOCUMENTS

PP28,077 P3 6/2017 Byrne et al.

OTHER PUBLICATIONS

U.S. Appl. No. 19/336,141, filed Sep. 22, 2025, Byrne et al.
U.S. Appl. No. 19/336,148, filed Sep. 22, 2025, Byrne et al.
U.S. Appl. No. 19/336,164, filed Sep. 22, 2025, Byrne et al.
U.S. Appl. No. 19/336,169, filed Sep. 22, 2025, Byrne et al.
U.S. Appl. No. 19/336,361, filed Sep. 22, 2025, Byrne et al.
U.S. Appl. No. 19/336,363, filed Sep. 22, 2025, Byrne et al.
U.S. Appl. No. 19/336,365, filed Sep. 22, 2025, Byrne et al.
U.S. Appl. No. 19/336,368, filed Sep. 22, 2025, Byrne et al.
U.S. Appl. No. 19/336,370, filed Sep. 22, 2025, Byrne et al.
U.S. Appl. No. 19/336,372, filed Sep. 22, 2025, Byrne et al.
U.S. Appl. No. 19/336,375, filed Sep. 22, 2025, Byrne et al.
U.S. Appl. No. 19/336,377, filed Sep. 22, 2025, Byrne et al.
U.S. Appl. No. 19/336,380, filed Sep. 22, 2025, Byrne et al.
U.S. Appl. No. 19/336,383, filed Sep. 22, 2025, Byrne et al.
U.S. Appl. No. 19/336,385, filed Sep. 22, 2025, Byrne et al.
Rouse and Sherman. 1989. 'TropicBeauty': A low-chilling peach for subtropical climates. HortSci. 24(1): 165-166.

*Primary Examiner* — Kent L Bell
(74) *Attorney, Agent, or Firm* — Dentons US LLP

(57) ABSTRACT

Disclosed is a new variety of *Prunus persica* named 'TRH2E121L'. This new variety, which requires approximately 450 chilling units of dormancy, is considered to be a peach tree of early mid-season maturity, which produces yellow-fleshed, subacid, semi freestone fruit that are firm, with a 60-90% dark red-orange blush over a yellow ground color, and suitable for fresh market use.

5 Drawing Sheets

Latin name of the genus and species of the plant claimed: *Prunus persica.*

Variety denomination: 'TRH2E121L'.

BACKGROUND OF THE INVENTION

This invention relates to a peach tree and, more specifically, to a peach tree referred to as a variety of *Prunus persica* named 'TRH2E121L', which requires approximately 450 chilling units of dormancy, produces firm, semi-freestone, subacid, yellow-flesh peach with a 60-90% dark red-orange blush over a yellow ground color that matures in the early mid-season. The present peach tree was the result of an ongoing Stone Fruit Breeding Program at College Station, Brazos County, Texas. To this end, controlled crosses were made each year to produce seedling populations from which improved progenies are evaluated and selected. The seedling 'TRH2E121L' was derived from a cross between a low-chill, yellow-flesh, acid, peach selection 'TX2B136' (not patented) and a low chill, subacid, white-fleshed nectarine, 'Smooth Delight One' (patented). 'TX2B136' was a seedling selected from a cross between the low chill cultivar 'Hermosillo' (Sherman, W. B., J. Rodriguez-Alcazar, and B. L. Topp. 1992. Peaches and nectarines developed but not introduced by the University of Florida. Fruit Varieties Journal 46:124-127, not patented) and the low chill peach selection 'TXW1293-1' (not patented). 'TXW1293-1' was a low-chill peach selected from a large open pollinated population of seedlings with 'Tropic Beauty' (Rouse, R. E. and W. B. Sherman. 1989. 'Tropic-Beauty': A low-chilling peach for subtropical climates. HortSci. 24(1): 165-166, not patented) as the female parent. The seed from the cross between 'TX2B136' and 'Smooth Delight One' were embryo cultured and planted in 2011 in an experimental plot in Floresville, TX. 'TRH2E121L' was marked for subsequent observation in 2013 and noted as having exceptional characteristics.

'TRH2E121L' was bud grafted onto virus-free 'Nemaguard' (not patented, The Brooks and Olmo Register of Fruit and Nut Varieties, 3rd Ed., American Society of Horticultural Science Press, Alexandria, VA, 1997) peach at the nursery site in Oakdale, CA. The variety was subsequently planted and evaluated as two-year and older trees in Pleasanton (2018-2019), Somerville (2016-2020) and Fairfield (2015-2020), Texas. This evaluation clearly demonstrated that the re-propagated trees were true to the characteristics of the original seedling in all observable aspects.

SUMMARY OF THE INVENTION

The 'TRH2E121L' peach produces yellow-fleshed, subacid fruit that ripens in the early mid-season and which is firm and has a 60-90% dark red-orange blush over a yellow ground color. In this regard, the present variety of peach tree bears fruit that are ripe for commercial harvesting and shipment in late May to early June, when the fruit is grown in the medium chill zone of Texas. 'TRH2E121L' blooms ~13 days after its female parent 'TX2B136' (not patented) and ~2 days after its pollen parent 'Smooth Delight One' (patented, U.S. Plant Pat. No. 28,077)). It ripens 3-4 weeks after its parents. 'TRH2E121L' differs from its yellow-fleshed, acid, peach female parent as it has subacid flesh and differs from its white-fleshed, subacid nectarine pollen parent as it is a yellow-flesh peach. This new subacid, yellow-flesh peach exhibits potential to be commercialized in regions that have chilling accumulation that are relatively low.

'TRH2E121L' as compared to the medium chill white-fleshed subacid peach cultivar 'White Delight Two' (not patented, US App. Publication No. 2016/0205832 P1, abandoned) has yellow flesh versus white flesh, has a showy flower versus a non showy flower, has reniform glands versus globose glands, requires 100 less chill units to fruit well, and blooms about 2 weeks earlier than 'White Delight Two'. 'TRH2E121L' as compared to the medium chill peach cultivar 'Texking' (patented, U.S. Plant Pat. No. 14,627), it has a low acid versus a traditional acid flavor, has reniform versus globose glands, and ripens 2½ weeks later than 'Texking'. 'TRH2E121L' as compared to 'TRH3C111' (U.S. Ser. No. 19/336,377) a selection with the same parentage, blooms about a week later (February 17 versus February 9) and requires 150 more chill hours to fruit than 'TRH3C111'.

BRIEF DESCRIPTION OF THE DRAWINGS

This new variety of peach tree is illustrated by the accompanying photographs of plants in their fifth leaf grown in Pleasanton, Texas, as provided in FIGS. 1-5. These photographs show the plant's typical fruit, foliage, and flowers, and the colors shown are as true as can be reasonably obtained by conventional photographic procedures.

DETAILED BOTANICAL DESCRIPTION

Figure 1:
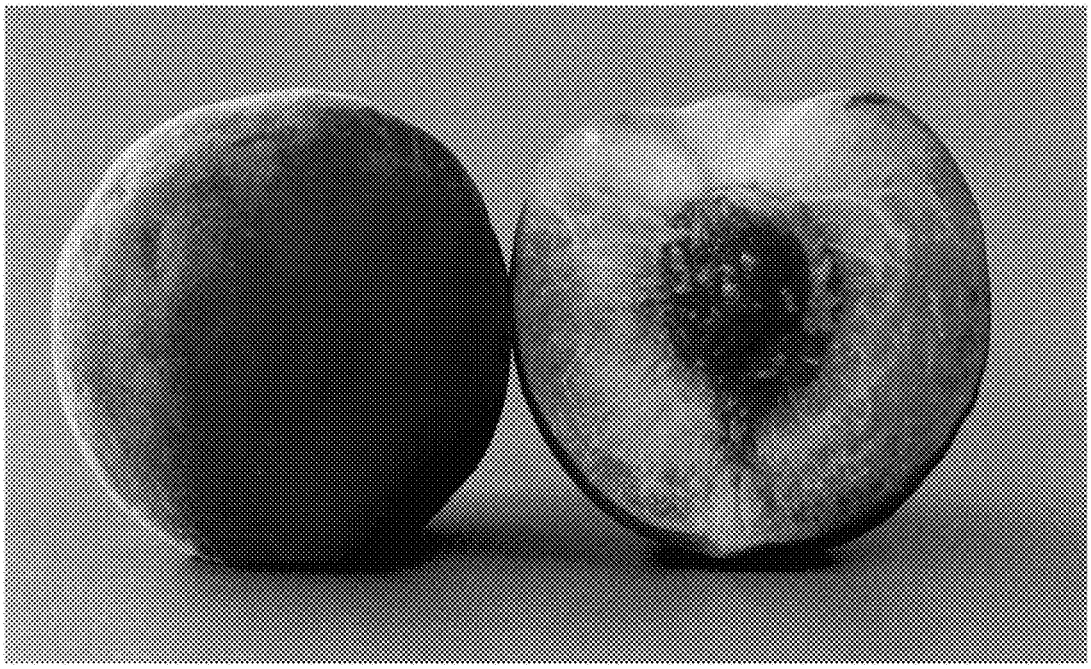
FIG. 1 Fruit of 'TRH2E121L' produced in Pleasanton, Texas showing external and internal coloration.
Figure 2:
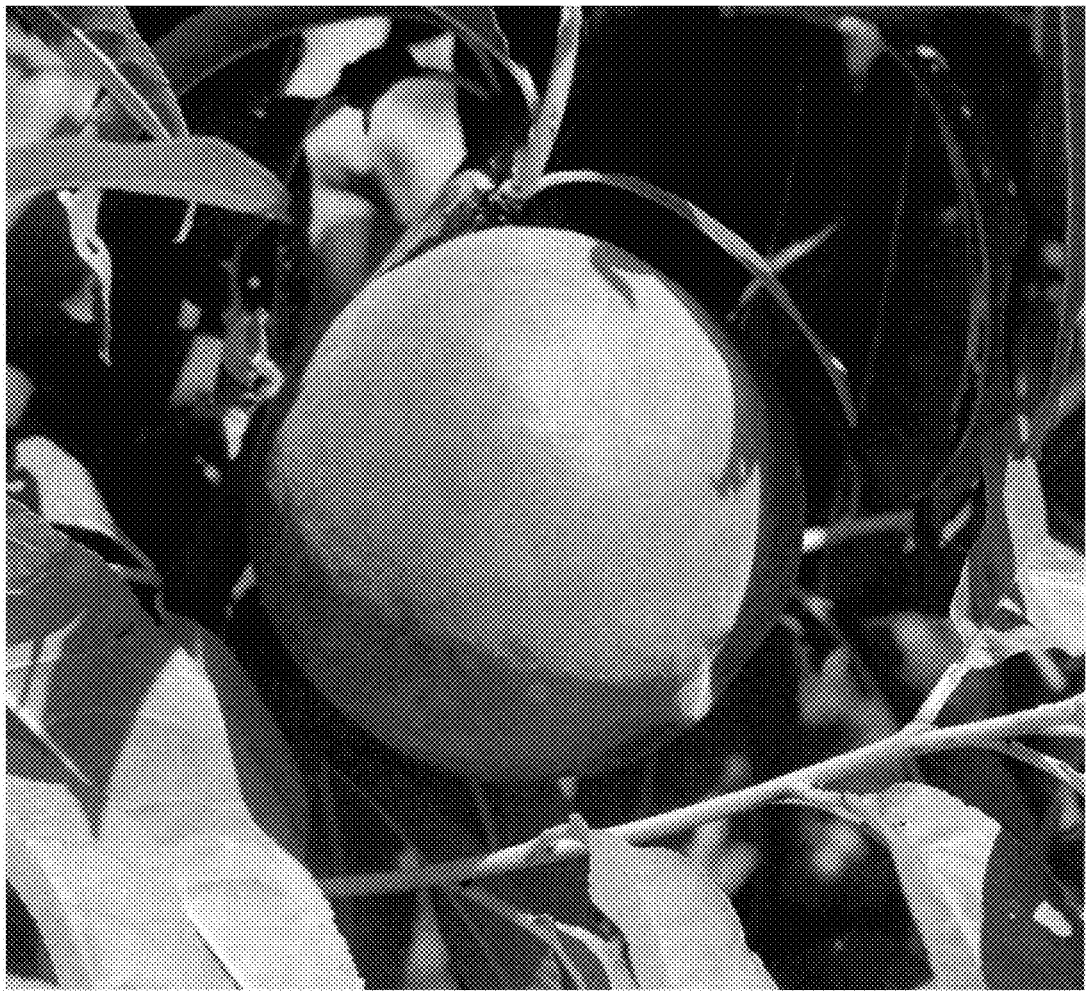
FIG. 2 'TRH2E121L' fruit produced in Pleasanton, Texas.
Figure 3:
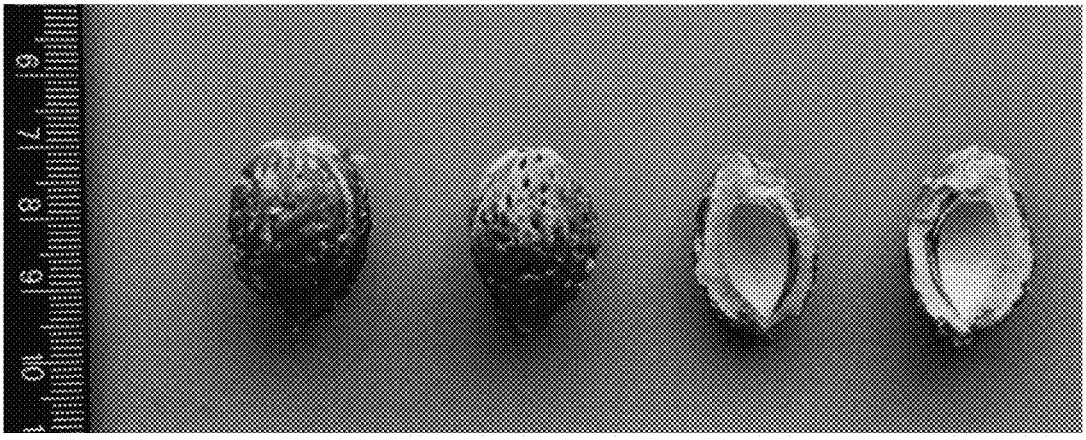
FIG. 3 Photograph of the endocarps of the 'TRH2E121L' peach. The ruler is in centimeters.
Figure 4:
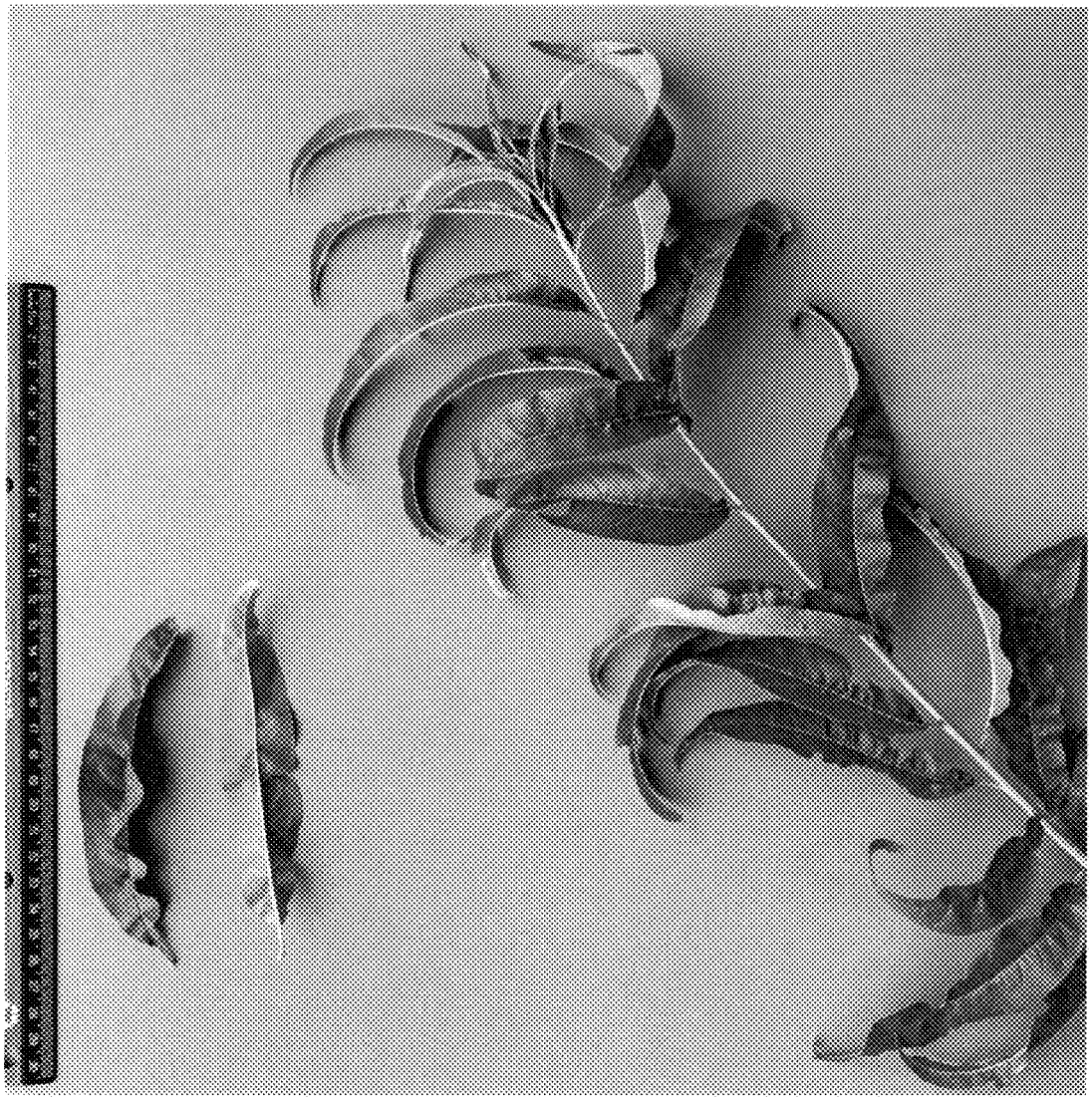
FIG. 4 A stem showing the leaves of the 'TRH2E121L' peach. The ruler is in centimeters.
Figure 5:
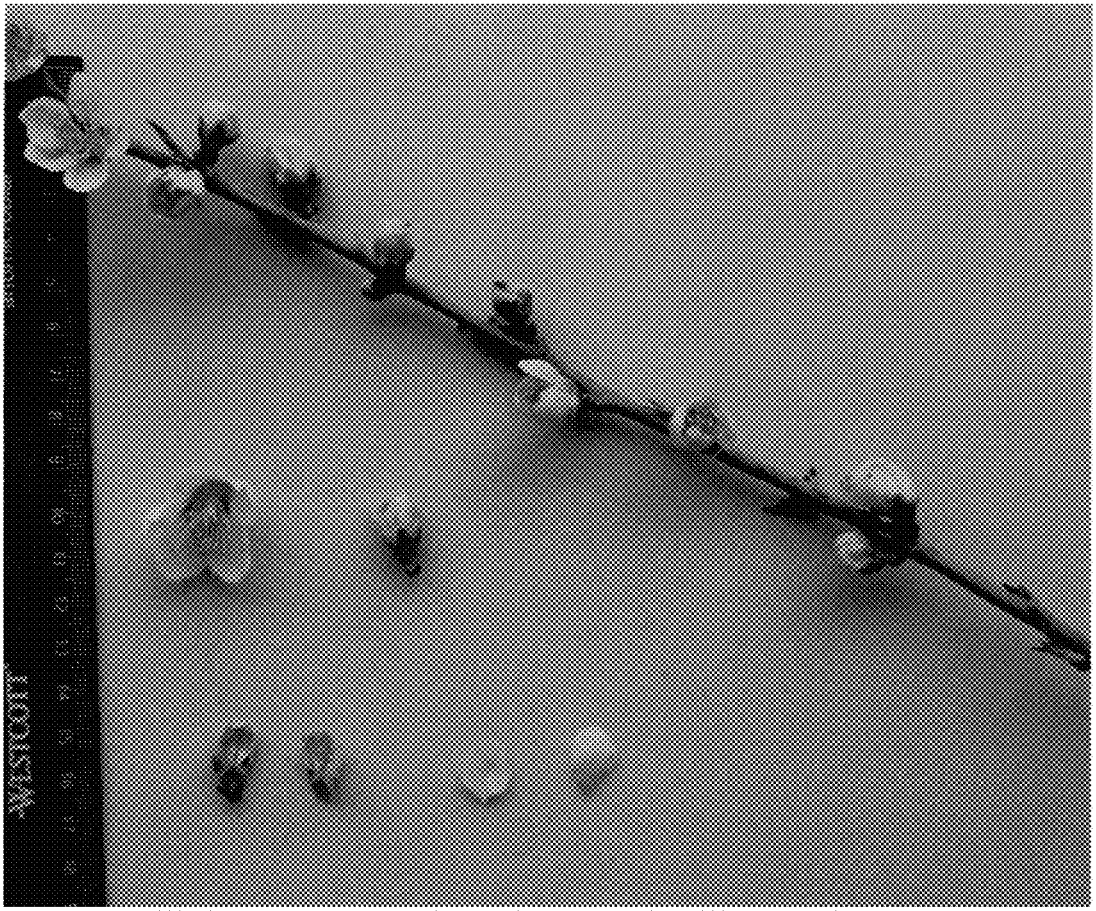
FIG. 5 A stem showing the flowers of the 'TRH2E121L' peach. The ruler is in centimeters.

Referring more specifically to the pomological details of this new and distinct variety of peach tree, the following has been observed under the ecological conditions prevailing at the experimental orchards in the medium chill zone of Texas (Pleasanton, Fairfield and Somerville). All major color code designations are by reference to The R.H.S. Colour Chart (2001 Edition) provided by The Royal Horticultural Society of Great Britain. Colors are approximate as color depends on horticultural practices such as light level and fertilization rate, among others.

Tree:

*Size*.—Generally medium to medium-high as compared to other common peach cultivars ripening in the medium chill zone.

*Height*.—6.6 to 8.2 feet (2 to 2.5 m) at the end of the 2020 growing season.

*Width*.—5.2 to 7.5 feet width (1.6 to 2.3 m) at the end of the 2020 growing season.

*Productivity*.—Produces annually in the medium chill zone of Texas without alternate bearing if temperatures of 28° F. or lower are not experienced during bloom. Trees are self-fertile and must be fruit thinned most years to avoid limb breakage and obtain optimal fruit size. The recommended fruit spacing for early to mid-season ripening fruit cultivars to yield a full crop is one fruit every 6-8" of one-year old fruiting wood. Trees often set more fruit than needed for a full crop.

*Shape*.—The 'TRH2E121L' peach has been trained in an open center configuration but exhibits a semi spreading growth type as seen in peach varieties 'Texprince' (patented, U.S. Plant Pat. No. 14,629) and 'Texking' (patented, U.S. Plant Pat. No. 14,627).

*Current season growth*.—The current season growth for the new variety was approximately 3.3 to 5 feet (1 to 1.5 m). Medium high to high vigor as compared to other commercial cultivars in the medium chill zone of Texas.

*Regularity of bearing*.—Regular in the absence of temperatures below 28° F. during bloom and considered hardy in the medium chill zone of Texas.

Trunk:

*Size*.—Approximately 1.75 to 3 inches (4.4 to 7.6 cm) in diameter and 5.5 to 10 inches (14 to 25.4 cm) in circumference when measured at a distance of approximately 12 inches (30.5 cm) above the soil level, at the end of the 2020 growing season on a three-year old tree.

*Bark texture*.—Considered moderately rough with numerous folds of papery scarf-like skin being present.

*Branches*.—Bark Coloration — Variable, colors (RHS2001) present are 166A, 172A, 172B, 173A, 175A, 175B and 176A of the Greyed-Orange Group, N200D of the Brown Group and 201D of the Grey Group.

*Thickness*.—Less than average (about 1 to 2 cm in diameter as measured 10 cm from the trunk on a three-year old tree) as compared to other varieties.

*Surface texture*.—Average and appearing furrowed on wood that is several years old.

*Lenticels*.—Numerous flat, oval lenticels present. The lenticels range in size from approximately 3 to 6 mm in width and were approximately 2 mm in height.

*Current season shoots*.—Surface texture-Substantially glabrous.

*Internode length*.—Approximately 2.0 to 3.1 cm as measured in the middle of a current season stem.

*Color of mature branches*.—The predominant colors (RHS2001) are 166B, 166C, 172A, 173A, 174A, 175A and 175B of the Greyed-Orange Group, N200D of the Brown Group and 201D of the Grey Group.

*Current season shoots*.—Color (RHS2001) — Light green (N144C of Yellow-Green Group) with some reddish-brown coloration appearing on exposed surface of the shoots (165A and 166A of the Greyed-Orange Group and 183A, 183B, 187A, 187B and 187C of the Greyed-Purple Group).

Leaves:

*Size*.—Considered moderately small for the species. Leaf measurements have been taken from vigorous upright current season growth approximately at mid-shoot.

*Leaf length*.—Approximately 112 to 136 mm.

*Leaf width*.—Approximately 26 to 38 mm.

*Leaf thickness*.—Approximately less than 1 mm.

*Leaf form*.—Lanceolate.

*Leaf tip form*.—Acuminate.

*Leaf upper surface color* (*RHS*2001).—Green varying among 137A, 137B of the Green Group.

*Leaf lower surface color* (*RHS*2001).—Green varying among 137C of the Green Group and 146A, 146B of the Yellow-Green Group.

*Leaf abaxial mid-vein color* (*RHS*2001).—Light yellow green (145C of the Yellow-Green Group).

*Leaf margins*.—Form — Considered crenate. Uniformity — Considered generally uniform. Texture — Glabrous.

*Leaf petioles*.—Length — Approximately 8 to 9 mm. Thickness — Approximately 1 to 1.5 mm. Texture — Glabrous. Color (RHS2001) — Pale green (144A and 145C of the Yellow-Green Group).

*Leaf glands*.—Size — Less than 1 mm in height and width. Number — Generally 0-1 per leaf. Type — Reniform. Color — Too small to determine.

*Leaf stipules*.—Length — Approximately 10 to 13 mm. Form — Lanceolate. Color (RHS2001) — Green, 144A, 144B, N144C, N144D, 145A, 146C and 146D of the Yellow-Green Group). Color is similar on both surfaces. The stipules are early deciduous. Ratio of flower buds to vegetative buds — Generally 2 flower buds per vegetative bud.

Flowers:

*Floral buds*.—General — The floral buds are conic in form, and slightly appressed relative to the bearing shoot. Color (RHS2001) — The mature floral buds are medium brown, (approximately 165A, 174A and 175A of the Greyed-Brown Group and 200D of the Brown Group). The buds are considered hardy in the medium chill zone of Texas. Mature Bud Length — 3 to 5 mm. Mature Bud Width — 1 to 2 mm.

*Blooming type*.—Mean date of full bloom in the medium chill zone of Texas was in mid-February (February 17$^{th}$ at Somerville and February 14$^{th}$ at Fairfield experimental plot), a few days before or with the commercial cultivars 'Texking' and 'Flordaking' (not patented, Andrews, C. P. 1979. 'Flordaking' peach. HortScience 14(1):81-82).

*Flower type*.—Showy.

*Flower size*.—Flower diameter at full bloom is approximately 27 to 30 mm.

*Bloom quantity*.—Considered abundant.

*Flower bud frequency*.—Generally 2 per node.

*Petal size*.—Width — Approximately 10 to 11 mm. Length — Approximately 16 to 17 mm.

*Petal form*.—Broadly ovate.

*Petal count*.—Generally 5.

*Petal color* (*RHS*2001) *abaxial/adaxial surfaces*.—Light to medium pink when young (65B, 65C, 65D, 69A, 69B and 73D of the Red-Purple Group and 75D of the Purple Group), becoming darker near the petal claw.

*Petal claw*.—Form — The claw is considered truncate in shape. Length — Approximately 1 mm. Width — Approximately 1 mm.

*Petal margins*.—Generally considered variable, from nearly smooth to slightly undulate.

*Petal apex*.—Generally — The petal apices appear rounded.

*Flower pedicel*.—Length — Average length of approximately 2 mm. Thickness — Approximately 1 to 1.5 mm. Color (RHS2001) — Medium green (144B, 144C, 144D, N144C, N144D, 145A and 145B of the Yellow Green Group).

*Floral nectaries*.—Color (RHS2001) — Medium to dark orange (25A, 25B, N25A, N25B, 28A and 28B of the Orange Group and N30D of the Orange-Red Group).

*Sepals*.—

*Number*.—Generally 5 sepals per flower. Surface Texture — The surface has a short, fine, wooly texture. Size — Average Width 3.6 mm, Length 4.3 mm Sepal form-Ovate. Color (RHS2001) — Maroon and green with white (approximately 59A, 59B, 60A and 60B of the Red-Purple Group; 144B, N144C and N144D of the Yellow-Green Group and 155A, 155B, 155C, 155D of the White Group).

*Floral cup* (*hypanthium*).—Surface Texture — Generally glabrous. Color (RHS2001) — Maroon with green (approximately 59A, 59B, 60A and 60B of the Red-Purple Group and 144B, N144C and N144D of the Yellow-Green Group).

*Anthers*.—Color (RHS2001) — Medium to dark orange (N25A, N25B, N25C, N25D, 28A and 28B of the Orange Group).

*Pollen production*.—Pollen is abundant and is a medium-dark yellow color (RHS2001) when dry (approximately 2A, 2B, 3A, 3B, 4A, 5A, 5B, 8A, 9A and 9B of the Yellow Group).

*Filaments*.—

*Size*.—Variable in length, approximately 10 to 14 mm, with the filaments being slightly shorter or equal to the pistil in length and shorter than the petals. Color (RHS2001) — White (approximately 155A, 155B, 155C, 155D of the White Group) and darkening with advanced maturity.

*Pistil*.—General — In general slightly taller or equal to the anther height and equal to or shorter than the petals. Length — Approximately 13 to 16 mm, including the ovary. Color (RHS2001) — Considered white to yellow-green when young (approximately 154C, 154D of the Yellow-Green Group and 155A, 155B, 155C, 155D of the White Group) and becoming slightly darker with advancing senescence.

Surface texture.—The variety has a pubescent style and ovary.

Fruit:

*Maturity when described*.—The present variety of fruit is described, as it would be found in its firm ripe condition at full commercial maturity. Under the ecological conditions prevailing in the medium chill zone of Texas it would be ripe in late May to early June. The average ripe date at Pleasanton, Somerville and Fairfield was May 27$^{th}$, June 4$^{th}$ and June 6$^{th}$ respectively

*Size*.—General — Medium large to large for the season and considered uniform. Average Cheek Diameter — Approximately 56 to 62 mm. Average Suture Diameter — Approximately 56 to 63 mm. Average Axial Diameter — Approximately 52 to 58 mm.

*Fruit form*.—Generally considered truncate with unequal halves. Occasionally the fruit exhibits less symmetry when comparing the suture height with the line opposite the suture. The fruit is generally uniform in symmetry when viewed from the apical aspect.

*Fruit suture*.—Generally, the suture appears as a thin line that extends from the base to the apex, and appears deeper at the apex, forming a shallow basin at the apical point. No apparent callusing or stitching exists along the suture line. Fruit suture depth at the midpoint is less than 1 mm. Color (RHS2001) — Dark red-orange. Approximately 34A, 34B, N34A, 35A of the Orange-Red Group and 42B, 42C, 46A, 46B and 53A of the Red Group.

*Ventral surface*.—Form — Considered uniform.

*Stem cavity*.—Width — Approximately 9 to 19 mm. Length — Approximately 21 to 29 mm. Depth — Approximately 8 to 12 mm.

*Fruit base*.—Round and flat.

*Fruit apex*.—Varies between flat, round and tapering.

*Fruit stem*.—Length — 8 to 10 mm. Thickness — Approximately 2 to 3 mm. Color (RHS2001) — Varies from light to medium green of the 144A, 144B, 144C, N144D, 145A, 145B and 146D of Yellow-Green Group.

*Fruit skin*.—Generally considered medium or average in thickness. Surface Texture — Light, short pubescence. Skin Acidity — Considered neutral. Tenacious to Flesh — Yes at commercial maturity. Tendency to Crack — Not observed. Skin Color — Generally — Variable, Marbled to solid pattern with approximately 60-90% of the fruit surface covered with an orange-red to maroon blush. Blush Color (RHS2001) — A dark red-orange color. Approximately N34A of the Orange-Red Group, 46A, 53A and 53B of the Red Group, 59A, 59B and 60A of the Red-Purple Group and 183A, 183B, N186C, 186A, 187B and 187C of the Greyed-Purple Group. Skin Ground Color (RHS2001) — 1A, 1B, 1C, 1D of the Green-Yellow Group and 3B, 3C, 4A and 4B of the Yellow Group.

*Flesh color* (*RHS*2001).—Light yellow-orange to medium yellow with red to dark pink flecks throughout the flesh. Approximately 13A, 13B, 13C of the Yellow Group, 14C, 14D, 15B, 15C, 15D, 16B, 16C, 16D and 18A of the Yellow-Orange Group, 45A of the Red Group and 67A and 61A, 63A and 67A of the Red-Purple Group. The intensity of the red to dark pink flecks in the flesh is medium to strong near the skin and weak to medium centrally and near the stone.

*Flesh fibers*.—These fibers are present throughout the flesh.

*Stone cavity color* (*RHS*2001).—Light yellow-orange to medium yellow with dark pink. Approximately 13A, 13B, 13C of the Yellow Group, 14C, 14D, 15B, 15C, 15D, 16B, 16C, 16D and 18A of the Yellow-Orange Group, 45A, 53B and 53C of the Red Group and N57A, 60A, 60B, 60C, 61A, 61B, 63A, and 67A of the Red-Purple Group.

*Flesh texture*.—Generally, the flesh is considered firm at commercial maturity.

Ripening.—Generally the fruit of the present variety ripens evenly.

*Flavor*.—Considered sweet (Brix 12-14) with a rich subacid flavor.

Stone:

*Attachment*.—Semi freestone at commercial maturity.

*Stone size*.—Length — Approximately 26 to 31 mm. Width — Approximately 18 to 22 mm. Thickness — Approximately 14 to 18 mm.

*Fibers*.—Generally a few fibers are attached sporadically over the surface of the stone.

*Stone form*.—Varies from elliptical to ovate.

*Stone base angle*.—The base angle of the stone is most frequently considered medium to wide.

*Stone apex angle*.—Varies from narrow to medium.

*Stone shape*.—Considered variable. The stone is normally ovoid to elongated.

*Stone surface*.—Surface Texture — Consists of single pits, rosettes of pits and chains of pits. Ridges — Numerous fine ridges are present basally and converge towards the base of the stone.

*Ventral edge*.—Considered variable, from small to medium to large.

*Dorsal edge*.—Shape — Grooved and having moderately rough edges.

*Stone color* (*RHS*2001).—The color of the dry stone is light brown with dark pink (59C, 60B, 60C, 60D, 61A, 61B, 61C, 64A and 67A of the Red-Purple Group, 161A, 161B, 161C of the Greyed-Yellow Group and 164B, 164C, 164D and 165D of the Greyed-Orange Group). The color of the inside surface of the endocarp is primarily 164C and 165D of the Greyed-Orange Group.

*Tendency to split*.—Splitting is relatively uncommon.

*Kernel*.—The ovate kernel fills the endocarp at harvest and measures approximately 5-6 mm in thickness, 8-9 mm in width and 14-16 mm in length. When dried, the shriveled kernels measure approximately 3-4 mm in thickness, 8-9 mm in width, and 13-15 mm in length. The colors (RHS2001) of the shriveled kernels are primarily 165B and N167A of the Greyed-Orange Group.

*Use*.—The subject variety, 'TRH2E121L', is considered to be a peach tree of early mid-season maturity, which produces subacid, yellow-fleshed fruit which are very firm and have a 60-90% dark red-orange blush over a yellow ground color, and which are useful for the fresh market.

*Keeping quality*.—Average. Retains firmness and flavor after 14 days of refrigeration at 3-5° C.

*Resistance to insects and disease*.—No atypical resistances/susceptibilities were noted under normal cultural practices to date.

*Shipping quality*.—Average. Fruit does not develop internal breakdown and retains good firmness and eating quality after 14 days of refrigeration at 3-5° C.

Although the new variety of peach tree possesses the described characteristics when grown under the ecological conditions prevailing in the medium chill zone of Texas in Pleasanton, Somerville and Fairfield, it will be understood that variations of the usual magnitude and characteristics incident to the changes in growing conditions, fertilization, pruning, and pest control are to be expected.

What is claimed is:

1. A new and distinct variety of peach tree named 'TRH2E121L', as illustrated and described herein.

* * * * *